(12) United States Patent
Tessmer et al.

(10) Patent No.: US 11,693,024 B2
(45) Date of Patent: Jul. 4, 2023

(54) QUANTUM DOT MICROSCOPE APPARATUS COMPRISING A NANOSCALE SEMICONDUCTOR ON THE TIP OF A FIBER, A TUNNELING ELECTRICAL LEAD AND A CAPACITIVE ELECTRICAL LEAD ON THE FIBER

(71) Applicants: Board of Trustees of Michigan State University, East Lansing, MI (US); Wisconsin Alumni Research Foundation, Madison, WI (US)

(72) Inventors: Stuart Holden Tessmer, Okemos, MI (US); Eric William Goodwin, Dewitt, MI (US); Oleksandr Levchenko, Middleton, WI (US)

(73) Assignees: Board of Trustees of Michigan State University, East Lansing, MI (US); Wisconsin Alumni Research Foundation, Madison, WI (US)

( * ) Notice: Subject to any disclaimer, the term of this patent is extended or adjusted under 35 U.S.C. 154(b) by 107 days.

(21) Appl. No.: 17/493,998

(22) Filed: Oct. 5, 2021

(65) Prior Publication Data
US 2022/0120784 A1    Apr. 21, 2022

Related U.S. Application Data

(60) Provisional application No. 63/093,828, filed on Oct. 20, 2020.

(51) Int. Cl.
*G01Q 70/12* (2010.01)
*G01Q 60/22* (2010.01)
(Continued)

(52) U.S. Cl.
CPC .......... *G01Q 60/22* (2013.01); *G01N 33/588* (2013.01); *G01Q 60/16* (2013.01); *G01N 21/6458* (2013.01)

(58) Field of Classification Search
CPC ........ G01N 21/64; G01N 33/58; G01Q 20/00; G01Q 30/02; G01Q 60/38; G01Q 60/40;
(Continued)

(56) References Cited

U.S. PATENT DOCUMENTS 6,516,281 B1    2/2003  Wellstood et al.
7,151,244 B2 *  12/2006 Cheng ................ B23K 26/0624
                                                    250/201.3

OTHER PUBLICATIONS

Tao, M., et al., "A Method to Control the fabrication of Etched Optical Fiber Probes with Nanometric Tips," Journal of Optics 12 (2010) 015503.
(Continued)

*Primary Examiner* — Que Tan Le
(74) *Attorney, Agent, or Firm* — Harness, Dickey & Pierce PLC

(57) ABSTRACT

A quantum dot microscope apparatus is provided. A further aspect employs a tilted or tapered end or tip on a microscopic probe. Another aspect of the present apparatus employs a probe including a quantum dot with only one tunneling lead connected to a power source. A manufacturing aspect includes creating a tapered or asymmetrically shaped specimen-facing end of a probe where a quantum dot is located on the end. A further manufacturing aspect includes using focused ion-beam milling to create a tip or end of a quantum dot microscope probe.

23 Claims, 10 Drawing Sheets

(51) Int. Cl.
*G01N 33/58* (2006.01)
*G01Q 60/16* (2010.01)
*G01N 21/64* (2006.01)

(58) Field of Classification Search
CPC ........ G01Q 70/10; G01Q 70/12; G01Q 60/16; G01Q 60/18; G01Q 60/22
USPC .............................................. 250/201.3, 239
See application file for complete search history.

(56) References Cited

OTHER PUBLICATIONS

Pilevar, S., et al., "Focused Ion-Beam Fabrication of Fiber Probes with Well-Defined Apertures for Use in Near-Field Scanning Optical Microscopy," Applied Physics Letters, vol. 72, No. 24 (1998) 3133.

Tao, W., et al., "A low-temperature scanning tunneling microscope capable of microscopy and spectroscopy in a Bitter magnet at up to 34 T," Review of Scientific Instruments, 88, 093706 (Sep. 29, 2017).

"Helios NanoLab 400 / 400 S / 40 ML / 600 User Operation Manual," 1$^{st}$ Edition, FEI Co. (published Dec. 9, 2010).

"Instruction Manual, Auto 306 Vacuum Coater with Turbomolecular Pumping System, vol. 1—Installation and Maintenance Instructions," Issue G, Boc Edwards (published before Oct. 2020).

Heliox Brochure 4868, Oxford Instruments (published Feb. 2019).

Tessmer, S., et al., "Subsurface charge accumulation imaging of a quantum Hall liquid," Erratum, Nature 392, p. 51-54 (1998).

Urazhdin, S., et al., "A simple low-dissipation for cryogenic scanning tunneling microscopy," Review of Scientific Instruments, vol. 73, No. 2 (Feb. 2002).

Goodwin, E., et al., "Development of the Scanning Majorana Microscope," (poster presentation on Oct. 2018).

Goodwin, E., et al., Development of the Scanning Majorana Microscope (PPT presentation on Mar. 2019).

* cited by examiner

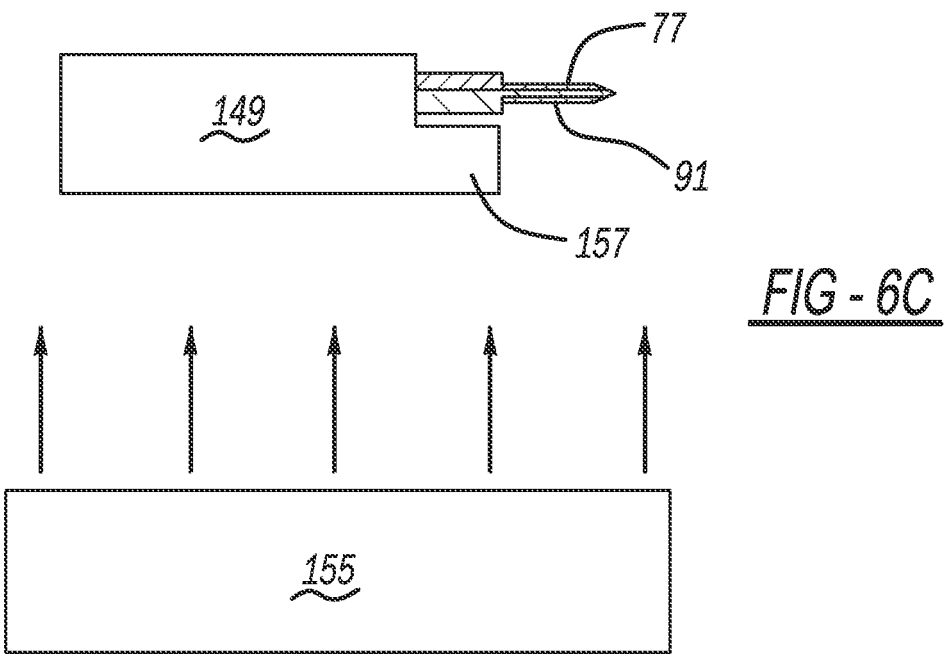
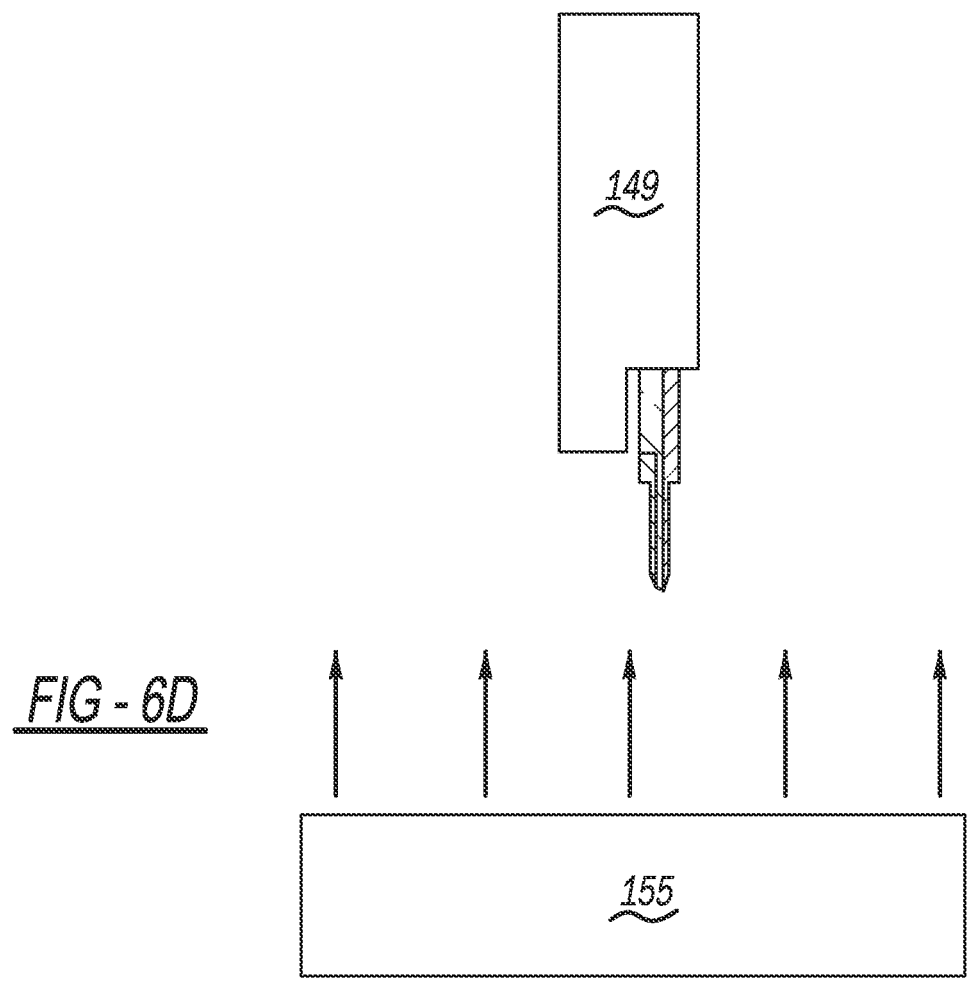

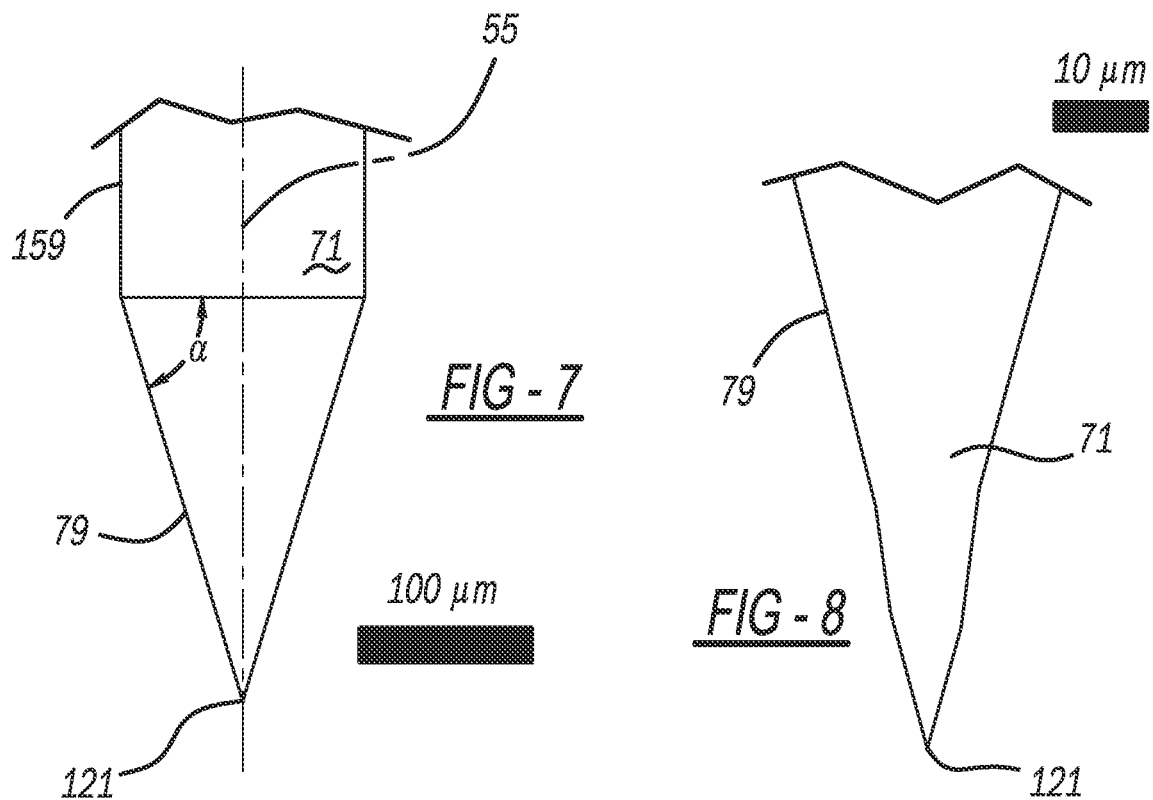
FIG-7
FIG-8
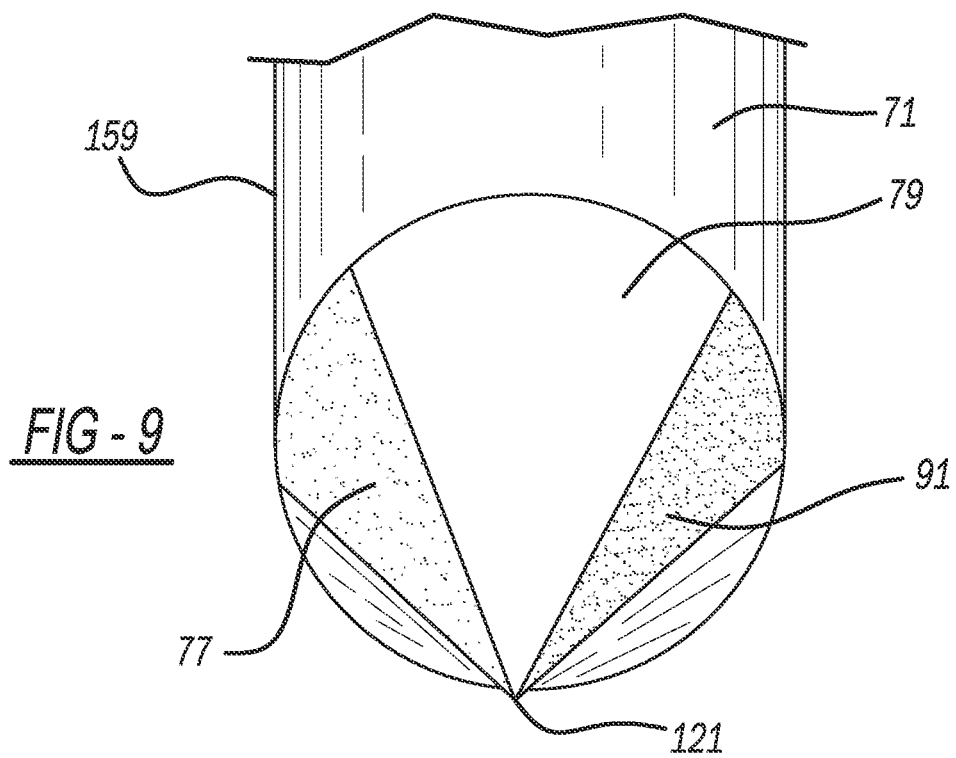
FIG-9

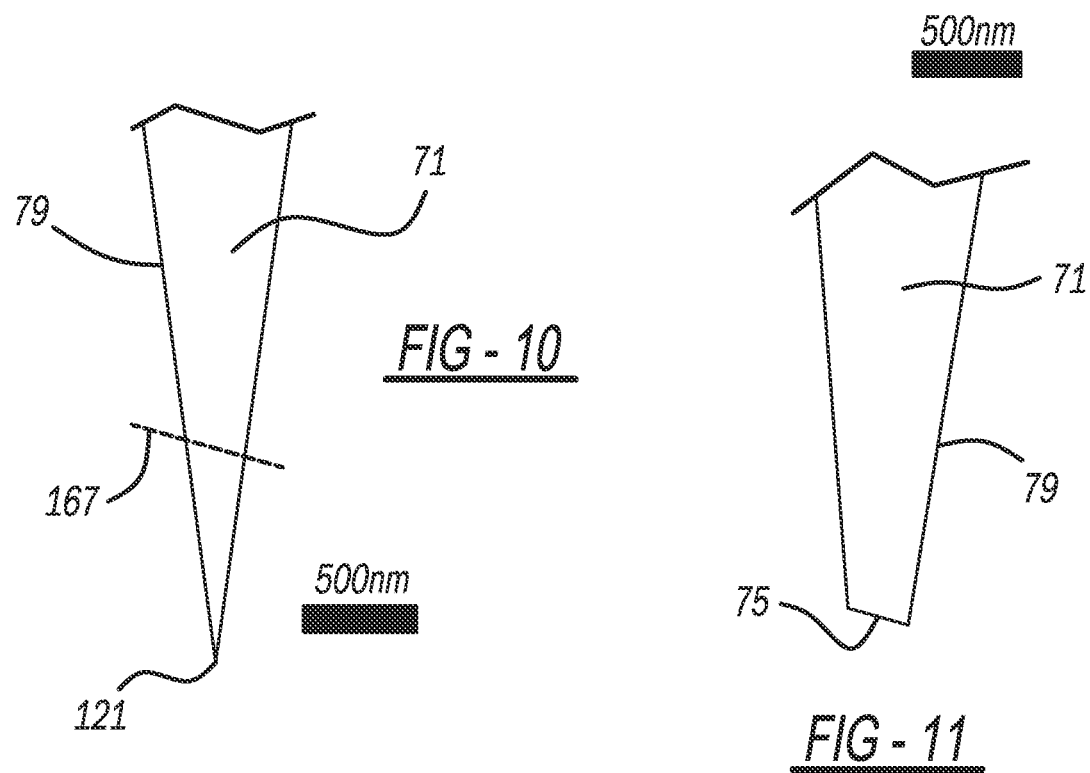
FIG - 10
FIG - 11
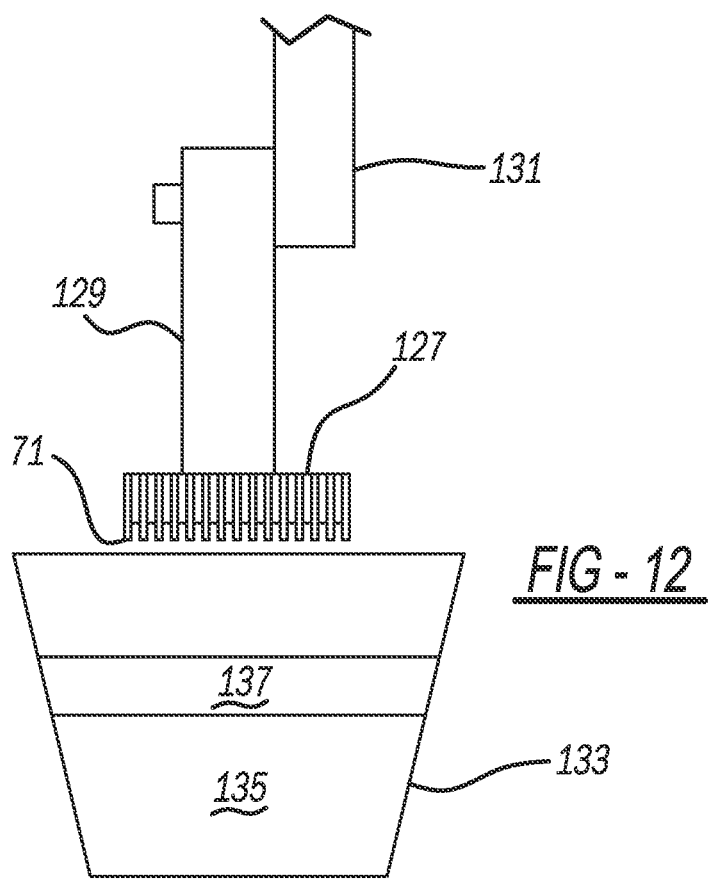
FIG - 12

QUANTUM DOT MICROSCOPE APPARATUS COMPRISING A NANOSCALE SEMICONDUCTOR ON THE TIP OF A FIBER, A TUNNELING ELECTRICAL LEAD AND A CAPACITIVE ELECTRICAL LEAD ON THE FIBER

CROSS-REFERENCE TO RELATED APPLICATIONS

The application claims the benefit of U.S. Provisional Patent Application Ser. No. 63/093,828, filed on Oct. 20, 2020, which is incorporated by reference herein.

GOVERNMENT SUPPORT

This invention was made with government support under DE-SC0017888 awarded by the U.S. Department of Energy. The government has certain rights in the invention.

BACKGROUND AND SUMMARY

The present application generally pertains to a microscope apparatus and more particularly to a probe of a quantum dot microscope apparatus.

A traditional near-field, Scanning Single Electron Transistor Microscope ("SSETM") is discussed in U.S. Pat. No. 6,516,281 entitled "Scanning Single Electron Transistor Microscope for Imaging Ambient Temperature Objects," which issued to Wellstood, et al., and is incorporated by reference herein. The SSETM device consists of a glass probe with two metallic leads and a quantum dot at an apex of the glass probe. This traditional method records the electronic transport passing entirely through the quantum dot, although not via capacitance. In order for the SSETM to operate, the two junctions must both allow electrical current flowing therethrough. Disadvantageously, tunnel junctions of this kind are very delicate and easily destroyed by contact with a sample. Given that there are two such tunnel junctions near the apex of the SSETM tip, the probe is highly sensitive to surface interactions. This damage concern forces the user to space the specimen 50-200 nm away from the probe, and this distance prevents the probe from strongly coupling.

In a different use, conventional chemical etching and Focused Ion-Beam ("FIB") fabrication of optical fiber probes are described in M. Tao, et al., "A Method to Control the fabrication of Etched Optical Fiber Probes with Nanometric Tips," Journal of Optics 12 (2010) 015503, and S. Pilevar et al., "Focused Ion-Beam Fabrication of Fiber Probes with Well-Defined Apertures for Use in Near-Field Scanning Optical Microscopy," Applied Physics Letters, vol. 72, no. 24 (1998) 3133. These known methods create an optical aperture in the end of a metal-coated fiber to allow light passage therethrough. The optical aperture surface is preferably flat and perpendicular to an elongated longitudinal centerline of the fiber, or has its furthest extending point symmetrically at the longitudinal centerline if the end is slightly convex, with a tangent to the aperture surface perpendicular to the fiber centerline. Thus, the end of the optical probe is not in close proximity to the specimen.

In accordance with the present invention, a quantum dot microscope apparatus is provided. A further aspect employs a tilted or tapered end or tip on a microscopic probe. Another aspect of the present apparatus employs a probe including a quantum dot or nanoscale semiconductor with only one tunneling lead connected to a power source. Still another aspect includes multiple, spaced apart, leads on a microscopic scanning probe; in one configuration, at least one of the leads may be a backgate lead, and in another configuration, two or more of the leads may be capacitive leads used to measure a quantum dot's thermodynamic density of states. Yet another aspect provides a microscopic scanning probe having a generally polygonal cross-section with substantially flat sides containing leads thereon.

A manufacturing aspect includes creating a tapered or asymmetrically shaped specimen-facing end of a probe where a quantum dot or nanoscale semiconductor is located on the end. A further manufacturing aspect includes using focused ion-beam milling to create a tip or end of a quantum dot microscope probe. Another manufacturing aspect creates a microscope probe having different layer thicknesses for an electrical current carrying lead, a capacitive lead and a quantum dot, all of which are on an insulating substrate.

The present sensor is advantageous over conventional devices. For example, the asymmetric and/or tapered tip of the present quantum dot microscope apparatus allows for a more robust probe capable of tunneling into a sample surface in the strong coupling regime. Moreover, the tilted design of the present tip advantageously allows positioning of the quantum dot very close to the sample surface while maintaining the tunneling junction a safe distance from the sample surface, thereby protecting the delicate tunneling junction. For example, the present apparatus allows the quantum dot to be positioned as close as 0.5 nm to the sample surface, which beneficially allows for strong probe interactions with states in the sample, while at the same time modifying tunnel charging of electrons into the quantum dot. In other words, with the present microscope apparatus, the electronic states in the quantum dot can overlap sufficiently to hybridize with electronic states in the sample. Thus, the present apparatus provides a strong-coupling quantum dot microscope. The present apparatus is also advantageously capable of single electron counting and angstrom distance tunneling. Furthermore, the present manufacturing methods are more accurate than conventional approaches. Additional advantageous and features of the present system and method will become apparent from the following description and appended claims, taken in conjunction with the accompanying drawings.

BRIEF DESCRIPTION OF THE DRAWINGS

FIGS. 6A-D are a series of cross-sectional views showing different manufacturing states of the probe of the present apparatus;

FIGS. 7 and 8 are side elevation views showing the probe of the present apparatus in an intermediate manufacturing state;

FIG. 9 is a perspective view showing the probe of the present apparatus in an intermediate manufacturing state;

FIG. 10 is a side elevation view showing the probe of the present apparatus in an intermediate manufacturing state;

FIG. 11 is a side elevation view showing the probe of the present apparatus in an intermediate manufacturing state after that of FIG. 10;

FIG. 12 is a diagrammatic view showing multiples of the probe of the present apparatus adjacent an etching tank;

DETAILED DESCRIPTION

Figure 1:
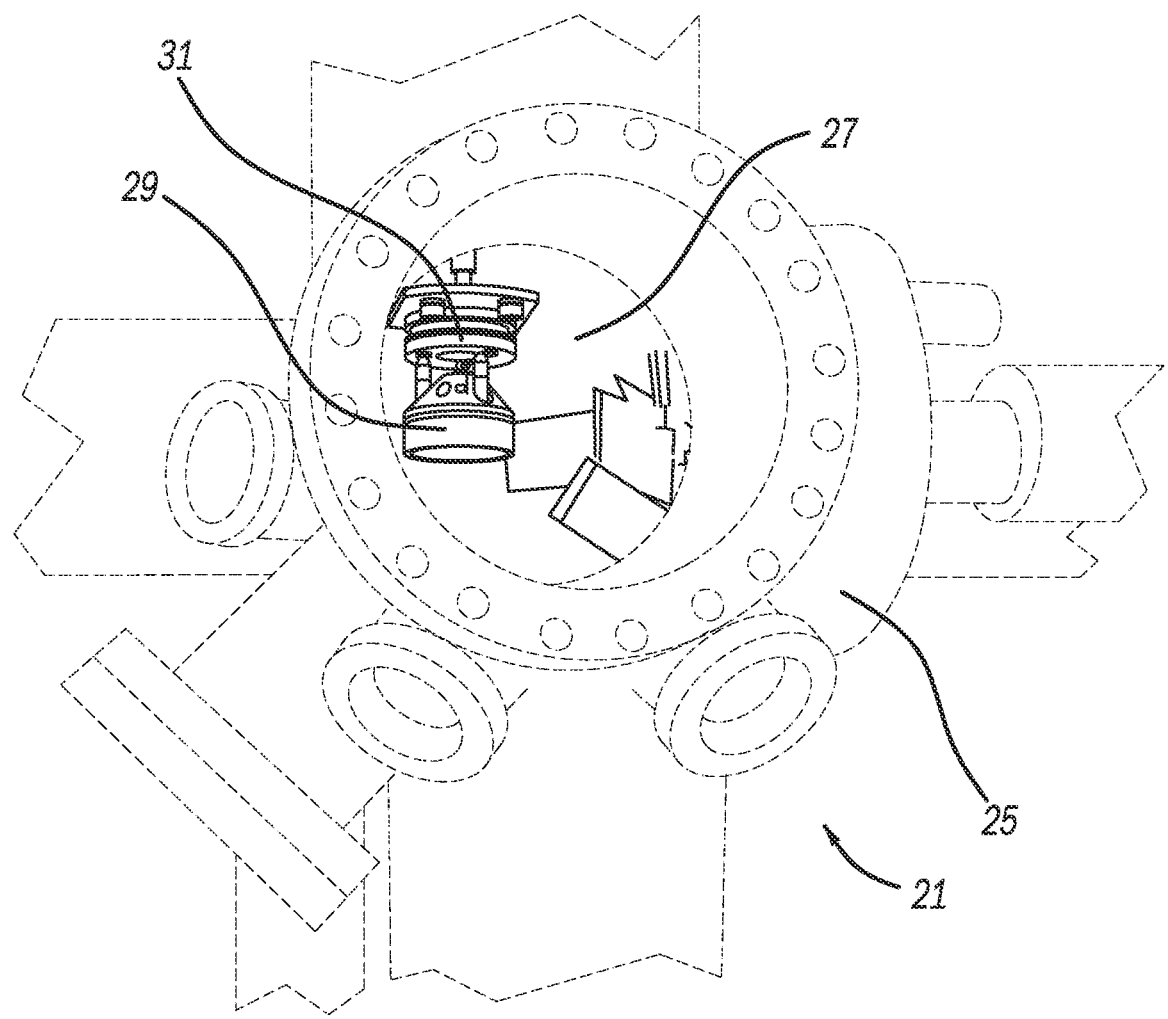
FIG. 1 is a perspective view showing the present quantum dot microscope apparatus within a cryogenic housing.
Figure 2:
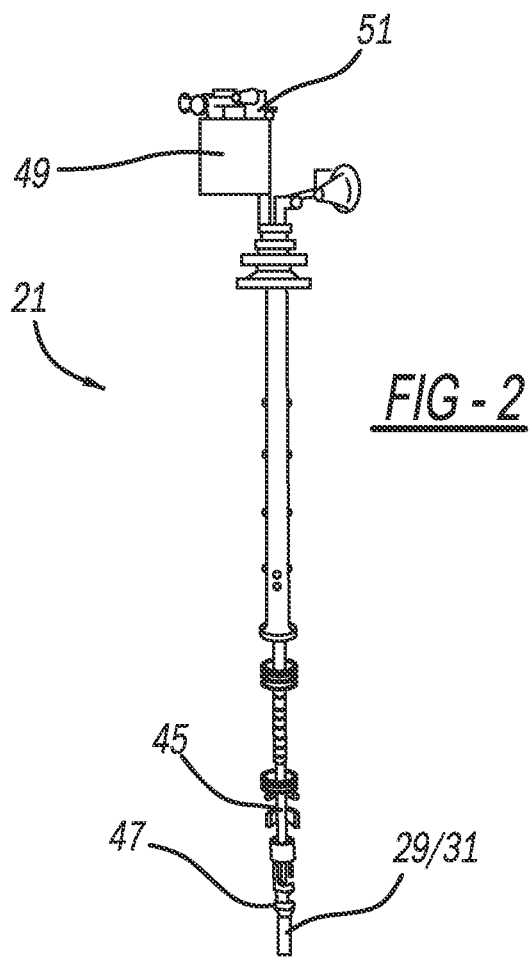
FIG. 2 is a perspective view showing a sorption pump for the present apparatus.
Figure 3:
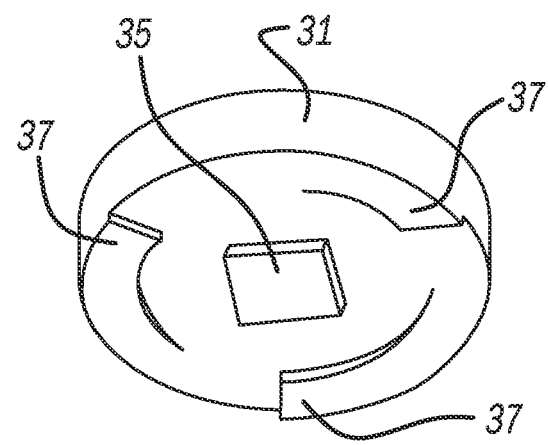
FIG. 3 is an exploded perspective view showing a sample holder and probe holder for the present apparatus.
Figure 3:
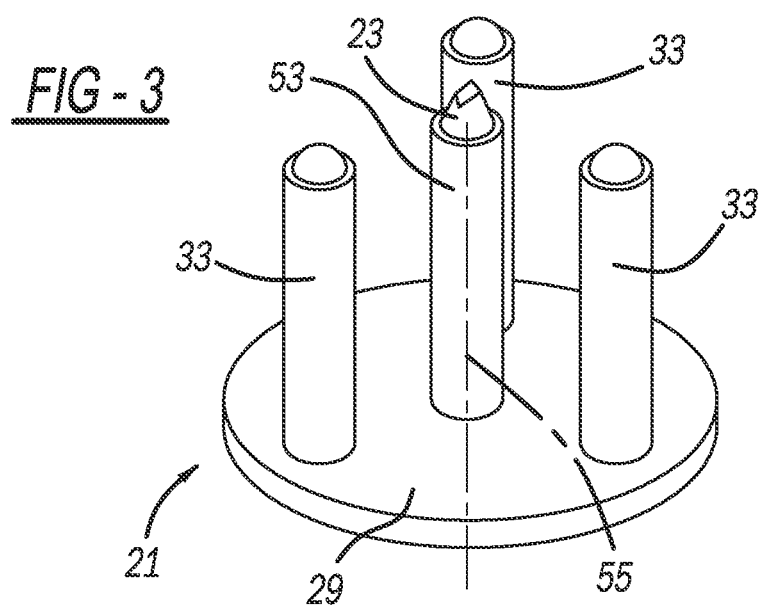

A preferred embodiment of a quantum dot microscope apparatus includes a probe having a tilted or tapered end or tip of a glass fiber. A quantum dot or nanoscale semiconductor is located on the tapered end. The scanning quantum dot microscope is capable of accessing single electron tunneling into the quantum dot with controllable coupling strength to surface states of interest. The preferred example of the probe used in the present strong-coupling quantum dot microscope is ultra-sharp with two electrical leads leading to an apex of a metallic quantum dot, connected to a charge-sensing circuit. An asymmetric tip design in conjunction with a capacitive sensing scheme provides access to the quantum dot's electron levels capable of operating within angstrom distance of the sample surface, while protecting a sensitive tunnel junction responsible for populating the quantum dot with electrons.

The present instrument is able to study localized surface states such as in Majorana Fermion systems used in constructing functional quantum computers. In one exemplary use, the scanning probe is used to study Majorana platforms or nanowires such as layered topological insulator and superconductor systems, iron-based superconductors, and magnetic chains. Moreover, Majorana zero modes, localized to superconducting vortex cores, benefit from the present moveable quantum dot probe.

The quantum dot used in the present apparatus is a mesoscopic island of metal or semiconductor with a quantized electronic level. The probe acts as an electrode. The capacitive charge sensing circuit provides the desired sensitivity for detecting electrons entering the quantum dot, able to record charge fluctuations on the order of $10^{-2} e^-/\sqrt{Hz}$. This charge sensitivity is achieved by connecting a quantum dot to a single tunnel junction which provides a capacitance measurement. Therefore, the single tunnel junction of the present probe enables surface tunneling with less risk for damaging the probe. By introducing an asymmetric tip design, by which the tunnel junction is positioned safely away from the surface, the sensitive tunnel junction is protected when the probe is positioned close enough to allow an angstrom distance for tunneling into the surface of the sample, such as less than 20 nm, and more preferably less than 1.0 nm, and most preferably 0.5 nm, from the specimen. The asymmetrical taper of an exterior surface of the quantum dot is also tilted at an offset angle relative to a nominal facing surface of the sample, resulting in the relatively insensitive capacitance lead being closest to the surface, reducing the effective tunneling area and further protecting the tunnel junction.

The microscope apparatus 21 and probe 23 will now be described in greater detail with reference to FIGS. 1-4. A housing 25 includes an interior cryogenic vacuum chamber 27 within which are located a scanning microscope head 29 and a specimen holder 31. Multiple piezo-electrically actuated walking tubes 33 longitudinally extend between head 29 and holder 31 and act in combination with multiple arcuate ramps 37, contacting against the tubes, to cause movement of a specimen or sample 35, retained by the holder, relative to probe 23. The specimen and holder 31 are shown vertically above microscope head 29 and probe 23, however, they may be inverted or in a horizontally aligned relationship depending on the microscope equipment employed.

An elongated rod longitudinally extends within a tube 41 partially located within a liquid Helium bath in chamber 27. A sorption pump is coupled to a dewar and head 29 is mounted near an end of the rod for retaining probe 23 thereto. A superconducting magnet surrounds an end of the tube and a condensing stage 45 is between the sorption pump and a lower Helium pot 47. Furthermore, a Helium dump 49 and a line-of-sight port 51 are at an opposite upper end. This configuration allows for the specimen to be at temperatures below 300 mK.

A central piezo-electric actuator 53 movably couples probe 23 to head 29 such that a longitudinal centerline 55 of probe 23 is aligned with specimen 35 with a gap 57 therebetween. Gap 57 is preferably less than 20 nm and greater than 0 nm, and more preferably less than 1.0 nm, and most preferably 0.5 nm. A nominal plane of an exterior surface 59 of specimen 35 is perpendicular to centerline 55 of probe 23.

Figure 4:
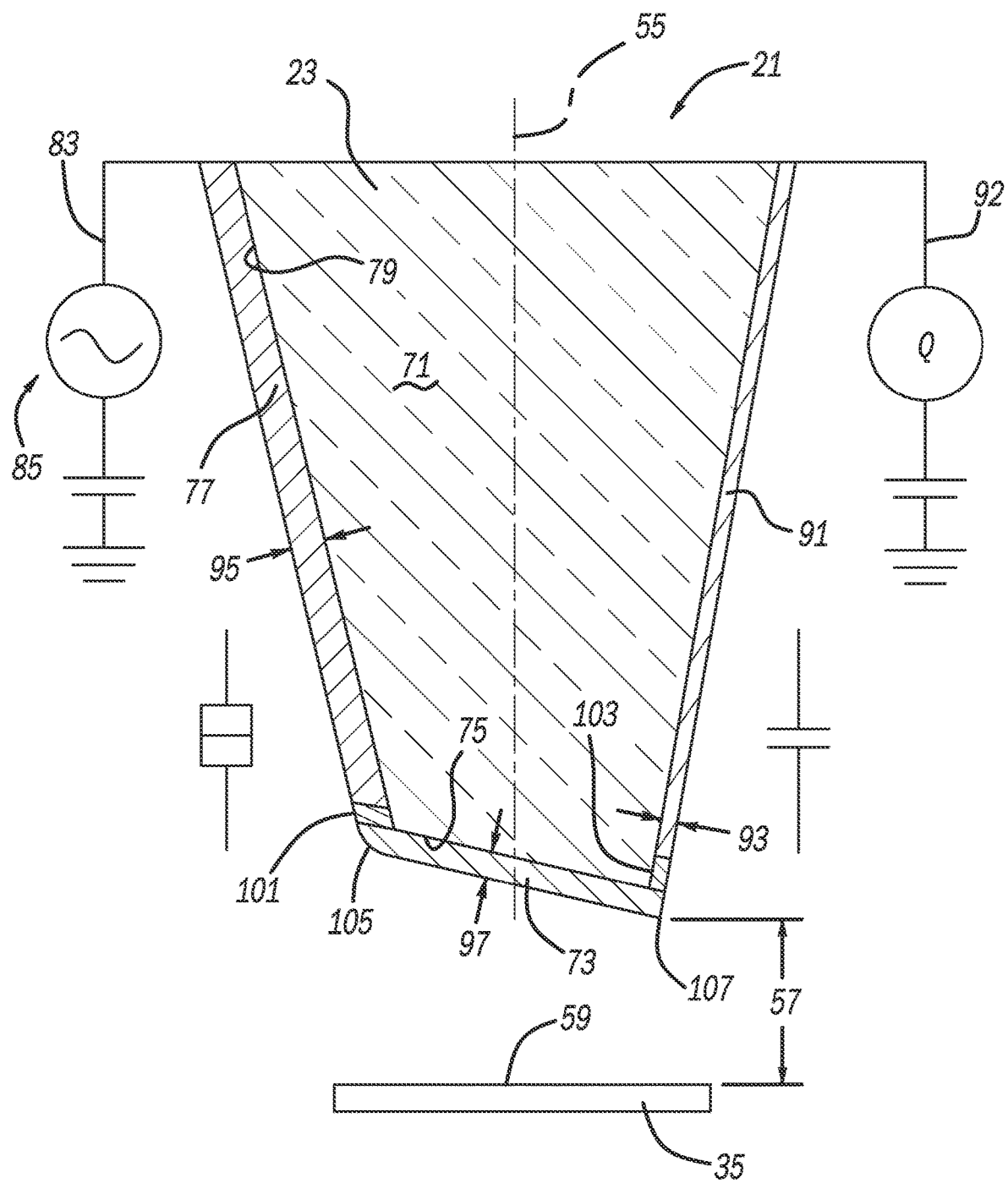
FIG. 4 is an enlarged cross-sectional view through the probe of the present apparatus, with the electrical circuits shown diagrammatically.
Figure 5A:
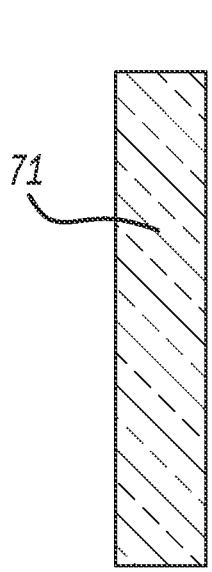
FIGS. 5A-F are a series of cross-sectional views showing different manufacturing states of the probe of the present apparatus.
Figure 5B:
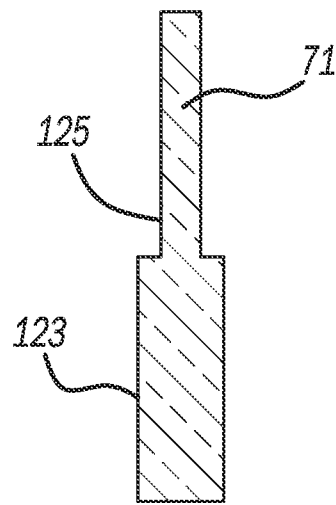
Figure 5C:
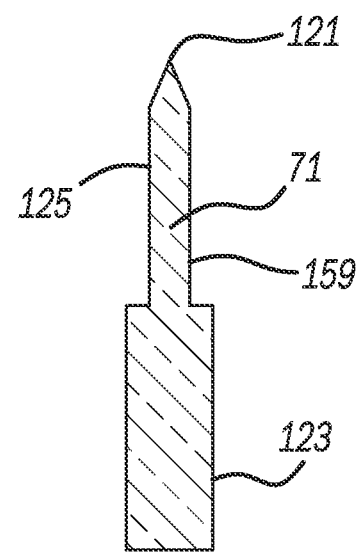
Figure 5D:
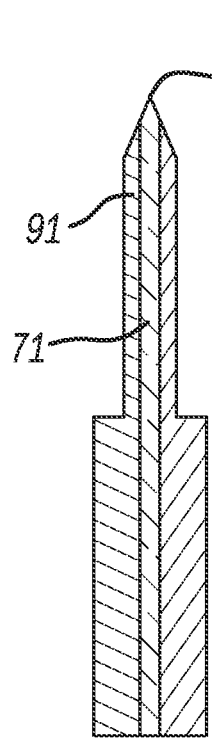
Figure 5E:
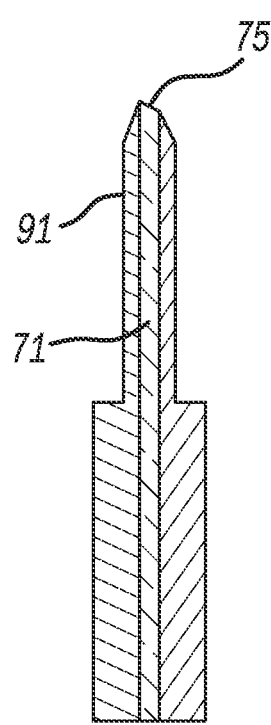
Figure 5F:
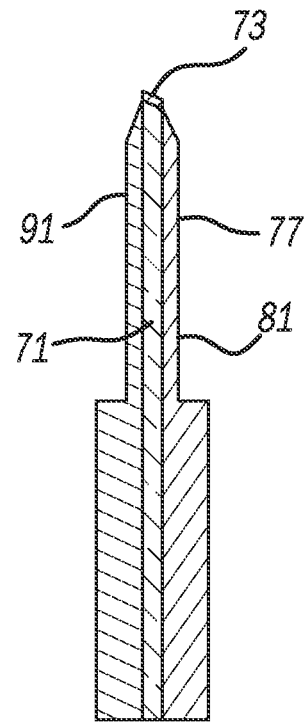

Referring now to FIGS. 4 and 5F, probe 23 includes a nonconductive, glass fiber or substrate 71 which is elongated along centerline 55. An aluminum quantum dot 73, having a generally circular peripheral edge, is located on the tapered distal end 75 of glass substrate 71. A powered and tunneling, electrically conductive lead 77 is locally located on a frusto-conical side surface 79, elongated in a direction between end 75 and a generally cylindrical, nominal section 81 of glass substrate 71. Tunneling lead 77 is part of an electrical circuit 83 connected to a DC power supply 85. Furthermore, a capacitive lead 91 is locally located on a generally opposite portion of side surface 79 of glass substrate 71. Capacitive lead 77 is elongated between end 75 and nominal section 81 of the glass substrate, and is part of a capacitive electrical circuit 92. The capacitive circuit is preferably similar to that disclosed in S. Urhzhdin, S. Tessmer and R. Ashoori, "A Simple Low-Dissipation Amplifier for Cryogenic Scanning Tunneling Microscopy," Rev. Sci. Instrum., vol. 73, no. 2 (February 2002) at 310.

Capacitive lead 91 is circumferentially spaced apart from tunneling lead 77. Capacitive lead 91 is also aluminum but has a cross-sectional dimension 93 thinner than a cross-sectional dimension 95 of tunneling lead 77. Moreover, both dimensions 93 and 95 are thinner than a cross-sectional dimension 97 of quantum dot 73. Alternately, leads 77 and 91 may alternately be gold or an alloy of aluminum or gold.

A tunneling junction 101 is located between and electrically connects quantum dot 73 to tunneling lead 77. Tunneling junction 101 is predominately aluminum oxide on the distal end of tunneling lead 77, but short enough to directly conduct some electricity from tunneling lead 77 to quantum dot 73.

An insulating junction 103 is located between capacitive lead 91 and quantum dot 73. Insulating junction 103 is predominately aluminum oxide on the distal end of capacitive lead 91, but is longer and thinner than tunneling junction 101 to create an electrical gap, thereby preventing electrical current from directly flowing from quantum dot 73 to capacitive lead 91. It is noteworthy that insulating junction 103 has a smaller cross-sectional area than does tunneling lead 77. Thus, capacitive lead 91 only receives the electrical field created by quantum dot 73.

In the present apparatus, a primary voltage is swept across the two leads, while a second voltage is maintained between the tip and sample. A capacitive measurement is employed that relies on the full counting statistics of the charge fluctuations of electrons entering the quantum dot at the apex of the tip. A DC voltage is swept between the tunnel and capacitance leads, 77 and 91, respectively. As the DC voltage is swept, electrons will tunnel from the tunneling lead onto quantum dot 73 at specific voltages, the spacing of which is dictated by the electrostatics of the quantum dot's environment. When an electron tunnels onto the quantum dot, an image charge is formed in the capacitance lead. Capacitance lead 91 is connected to a gate of a High Electron Mobility Transistor ("HEMT"), which amplifies this small change in charge in the capacitance lead into a measureable voltage across the HEMT's source/drain channel. In this way, charge is detected. An AC voltage of approximately 20 kHz is on top of the DC voltage. The AC excitation causes the electron to rapidly tunnel onto and off of the quantum dot as the DC voltage is swept past a value where the electron could tunnel. In turn, this oscillation produces an oscillating response in the image charge formed in the capacitance lead, resulting in a 20 kHz signal being applied to the gate of the HEMT, which also results in a 20 kHz signal across the source/drain channel. A lock-in amplifier is then used to extract the amplitude of the 20 kHz signal across the source drain channel, which is ultimately a measure of the change in capacitance of the quantum dot as a function of applied DC voltage.

The DC voltage, applied between the tunneling lead and the capacitance lead, is swept with an AC excitation voltage superposed. A balancing channel capacitively coupled to the tip serves to subtract the background signal due to stray capacitance and is tuned. As the DC voltage approaches a single electron addition level, lock-in techniques are used to track the single charge as it tunnels into and out of the quantum dot due to the AC excitation. Furthermore, the presence of a half-elliptical capacitance peak indicates single electron tunneling. Due to the small signal sizes, typically attofarads, the probe relies on repeated measurements and averaging to reduce ambient noise. Single electron peaks are generally identifiable after just a few minutes of averaging. Moreover, scanning controllers are used to provide voltage sweeps and pulse generators provide the excitation voltage. The digital delay and pulse generator serve as a trigger for the lock-in amplifier to lock in the correct frequency, they generate the desired AC excitation sent to the quantum dot to enable charge sensing, and they general a signal to reduce ambient charge noise form the environment as discussed hereinabove.

A peripheral corner 105 of quantum dot 73, adjacent to tunneling junction 101, is curved. Furthermore, this area of the quantum dot and the delicate tunneling junction are longitudinally recessed due to the taper angle of end 75 and quantum dot 73 thereon. In contrast, an opposite peripheral corner 107 of the quantum dot is generally a sharp intersection, and this area of quantum dot 73 and the adjacent capacitive junction 103 longitudinally project further than rounded corner 105 and tunneling junction 101 due to the taper angle. Accordingly, corner 105 of quantum dot and tunneling junction 101 are advantageously protected from undesirable contact against specimen 35 when there is movement of the probe relative to the specimen or vice versa. In other words, the more robust corner 107 will contact the specimen before the remainder of the quantum dot.

The manufacturing method and equipment will now be described. First, optical fiber 71, such as model SM-300 from Thorlabs, serves as an elongated and cylindrical substrate for the scanning probe, as shown in FIG. 5A. The optical fiber is cut to a desired length of approximately 2-5 cm. Referring to FIG. 5B, optical fiber 71 has three concentric layers: (a) a protective jacket 123, with a diameter of about 250 μm; (b) a fluorine-doped silica layer, with a diameter of about 125 μm; and (c) an innermost pure silica core 125. Jacket 123 is first removed on half of the cut optical fiber which exposes the fluorine-doped silica layer.

Referring now to FIG. 12, approximately forty of optical fibers 71 are then loaded into a Teflon® holder 127. Holder 127 preferably includes a circular and flat thermal evaporator plate to which multiple rectangular blocks are secured, the blocks having spaced apart holes for receiving fibers 71. Holder 127 is secured to a micropositioner 129, which is attached to a chemical ring stand 131 and placed in a fume hood. A Teflon® coated beaker 133 is filled with about 40 mL of 60% hydrofluoric acid 135. Furthermore, an immiscible layer of 80% oleic acid 137 is added on top of the hydrofluoric acid. Holder 127 is subsequently lowered into beaker 133 by micropositioner 129, until the exposed tips of fibers 71 are immersed in the hydrofluoric and Oleic acids. The fiber tips are thereby etched for about 38 minutes and 30 seconds. The holder and fiber tips are then removed from the etching solution and the fibers are sequentially cleaned with acetone, isopropanol and then deionized water.

After etching, sidewall 79 of each fiber's tip is generally conical with an apex diameter of approximately 100-200 nm, and a relatively steep sidewall 79 angle α of 70-85 degrees, and more preferably 76 degrees, from the cylindrical portion. FIG. 8 shows this enlarged from FIG. 7. The etched optical fibers are then removed from the holder, and placed into retainers, and baked at approximately 120 degrees C. for 10 minutes to remove any excess water left over from the cleaning step.

Figure 6A:
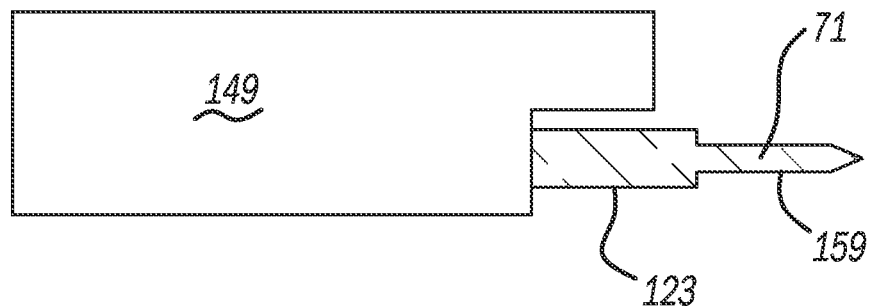
Figure 6B:
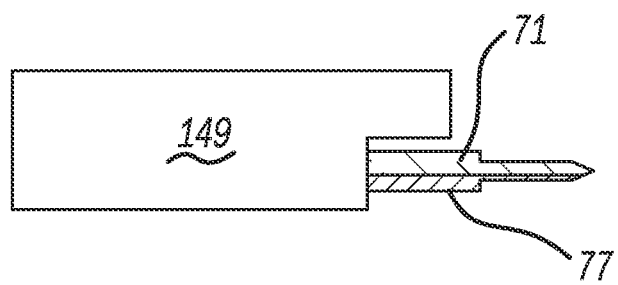
Figure 6B:
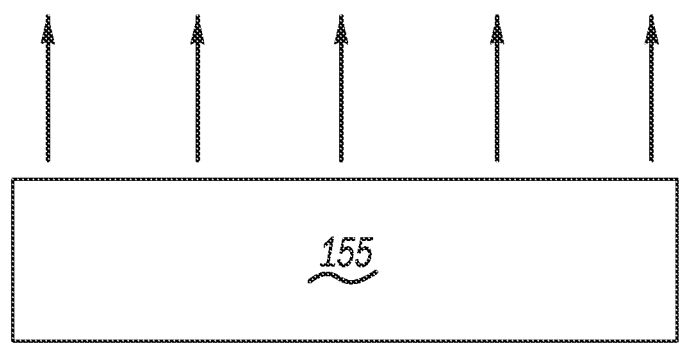
Figure 13:
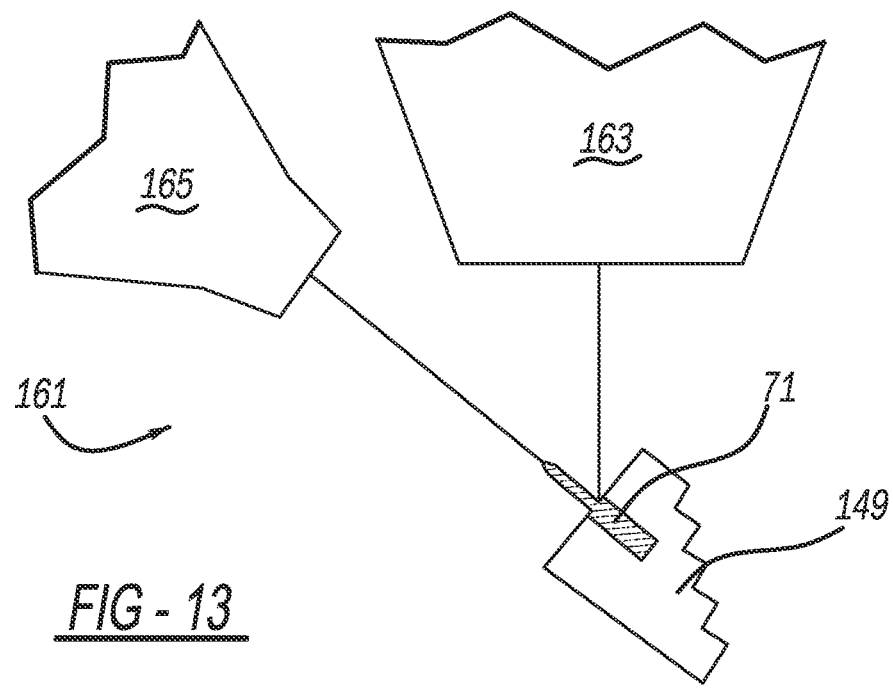
FIG. 13 is a diagrammatic view showing the probe of the present apparatus within an ion-beam milling machine.
Figure 14:
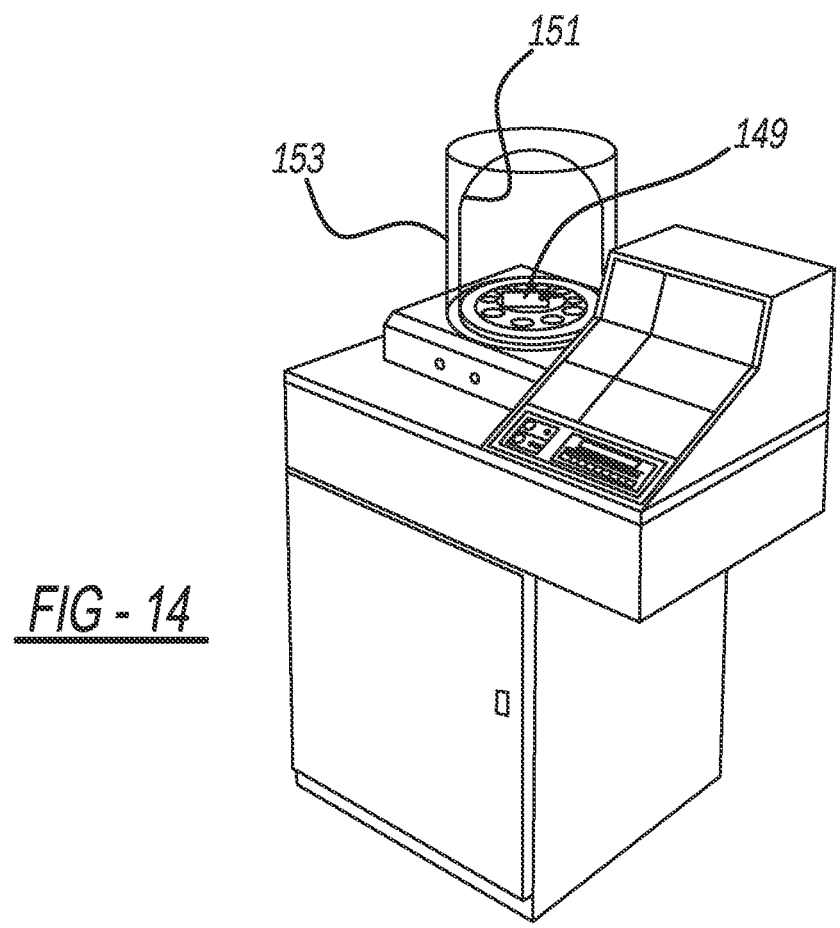
FIG. 14 is a perspective view showing the probe of the present apparatus within a coating machine.

Reference should now be made to FIGS. 5D, 6A-6D, 9 and 14. Retainers 149 and fibers 71 are then placed in a thermal evaporation chamber 151 of a cylindrical, stainless steel housing 153 for metal processing in a vacuum. One exemplary thermal evaporator is the Auto 306 vacuum coater with a turbomolecular pumping system which can be obtained from BOC Edwards of West Sussex, UK. 15-20 nm, and preferably approximately 16 nm, of Aluminum are evaporated onto one side of the probe at a rate of about 2.0 A/s to create tunneling lead 77, as is illustrated in FIG. 6B. Next, the vacuum is broken to allow air access to the partially coated fiber which causes a thin aluminum oxide skin of 3 nm or less, on the tunneling lead. The fibers 71 and their retainers 149 are then flipped 180 degrees to the orientation of FIG. 6C, the vacuum pressure is again created, and a thinner coating, such as 10-15 nm, of Aluminum from source 155 is thereafter evaporated on the opposite portion of sidewall 79 to create capacitive lead 91. Next, the vacuum is again broken to allow air access which causes a thin aluminum oxide skin of 3 nm or less, on the capacitive lead.

A stepped projection 157 of retainer 149 shields the underlying portion of fiber 71 from receiving the evaporating metal when the projection is between the fiber and the source 155. Due to the directionality of thermal evaporation, two symmetric and distinct leads are deposited in a generally triangular shape on opposite sides of conical sidewall 79 and on a longitudinally extending cylindrical sidewall 159 of the nominal length of the fiber. This pencil-like intermediate shape is advantageous since any deposited aluminum that does not land on the desired conical sidewall areas merely creates insulating aluminum oxide rather than electrically shorting the leads. The highly directional nature of the present thermal evaporation process and retention, as compared to techniques like sputtering, ensures two (or more) distinct electrical leads can be deposited on the glass fiber substrate without shorting.

Subsequently, scanning electron microscopy-based focused ion-beam milling ("FIBSEM") is utilized to create an asymmetrical offset angled taper between the two electrical leads, while also creating the distinct tunnel junction and capacitance junction. This is shown in FIGS. 4, 5E, 5F, 10, 11 and 13. An exemplary ion-beam milling machine is the FEI Helios Nanolab 650 which can be obtained from ThermoFisher Scientific. Retainer 149 and the metallic-coated fibers 71 are loaded into a FIBSEM machine 161. FIBSEM machine 161 includes a view window, an electron column 163 and an ion column 165. A 7 pA Ga ion beam is used to perform the mill with a cycle time of about 3-10 seconds per individual cut.

To achieve the desired asymmetric apex and taper of end 75, an ion emission and milling direction 167 are at a shallow angle from perpendicular to centerline 55, such as 1-5 degrees. FIG. 10 shows pointed tip 121 before ion milling and FIG. 11 shows tapered end 75 after ion milling. The small angle offset, in conjunction with a low ion beam current for a rectangular polishing cut (7 pA), results in a slight curve 105 at a corner which defines tunnel junction 101. The same tapered cut results in a flat area at end 75, which will host the quantum dot. Moreover, a periphery of the tapered cut end 75 is entirely within the pure silica core material. The opposite lead, which is not milled, defines capacitive junction 103. Further, the ion beam milling is used to shape the conical and end portions of the probe by removing non-uniformities and defects, as well as removing electrical shorts between the leads.

After the ion-beam milling, the metal coated fiber is again exposed to air which oxides the entire distal ends of leads 77 and 91 to create the junctions 101 and 103. Tunneling junction 101 is thicker, shorter and has a greater cross-sectional area than capacitive junction 103, such that while that tunneling junction is less conductive than a nominal portion of the integral lead 77, tunneling junction 101 still conducts some electricity between tunneling lead 77 and quantum dot 73. Furthermore, the aluminum oxide forming the longer length, thinner and smaller area capacitive junction 103 thereby makes it essentially insulative and non-conducting between quantum dot 73 and its integral capacitive lead 91. The angle of the FIB milling and the angular setup of the fiber within the deposition chamber also cause the tunneling junction to have a larger cross-sectional area and shorter length as compared to the capacitive junction.

FIGS. 5F and 6D show a subsequent end-on thermal evaporation step to create quantum dot 73 at the apex. This deposits or coats a thickness of about 7 nm of aluminum onto the tapered end 75 of glass fiber substrate 71 from deposition source 155. Owing to the steep incline of the taper, excess aluminum deposited on the leads in this step oxidize, to eliminate potential electrical shorts from this processing step. The excess aluminum that may deposit on the leads in this step is thin enough to oxidize to become insulating aluminum oxide, due to the steep angle of the tip. Finally, the metallized and milled probes are removed from the metal deposition machine, connected to a high electron-mobility transistor charge sensing circuit, and coupled to the present microscope apparatus.

Figure 15:
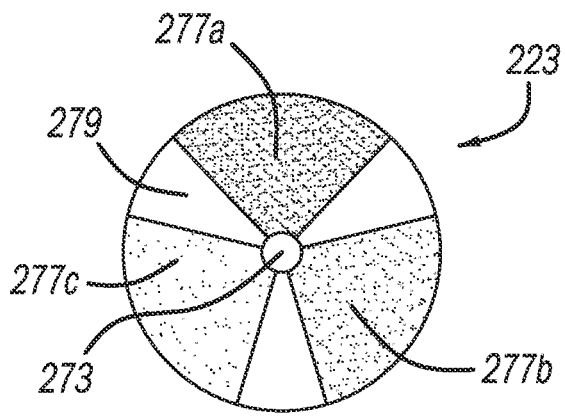
FIG. 15 is an end elevation view showing a first alternate embodiment of the probe of the present apparatus.
Figure 16:
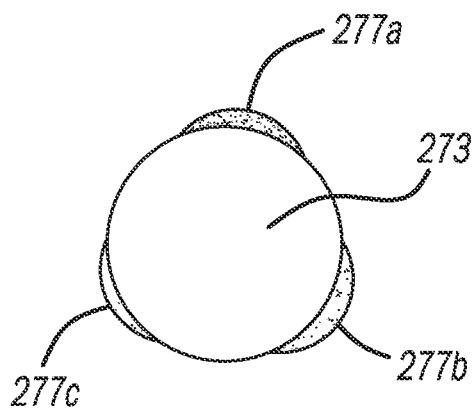
FIG. 16 is an enlarged end elevation view showing the first alternate embodiment of the probe of the present apparatus.

Reference should now be made to FIGS. 15 and 16 for an alternate embodiment of a probe 223 of the present apparatus. This exemplary probe 223 has three (or more) tunneling electrical leads 277a, 277b and 277c which are circumferentially spaced apart from each other on frusto-conical sidewall 279. These are preferably all electrically conductive leads with tunneling junctions between all of them and a centrally asymmetrically tapered quantum dot 273 located on an end or tip of a glass fiber substrate.

Figure 17:
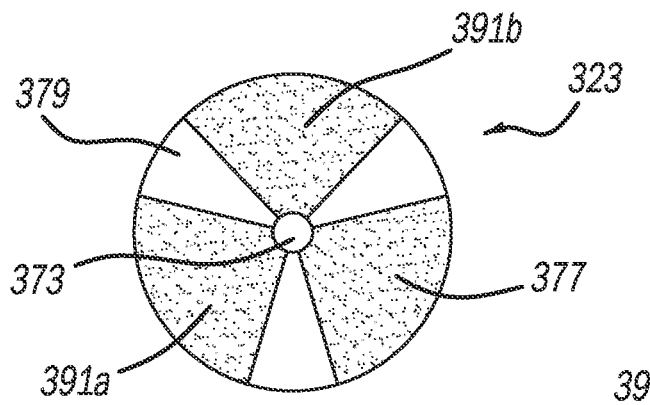
FIG. 17 is an end elevation view showing a second alternate embodiment of the probe of the present apparatus.
Figure 18:
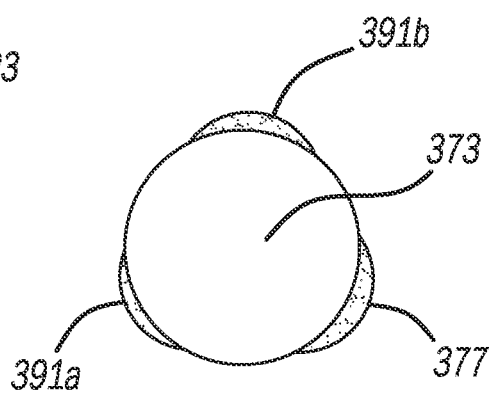
FIG. 18 is an enlarged end elevation view showing the second alternate embodiment of the probe of the present apparatus.

FIGS. 17 and 18 show another alternate embodiment of a probe 323 for the present apparatus. This exemplary probe 323 has two (or more) capacitive leads 391a and 291b which are circumferentially spaced apart from each other on frusto-conical sidewall 379. Lead 391b may be a backgate lead. A capacitive and insulating junction is located between each of these capacitive leads and a centrally asymmetrically tapered quantum dot 373 located on an end or tip of a glass fiber substrate. A powered and tunneling electrical lead 377 is also deposited onto conical sidewall 379, circumferentially spaced away from adjacent capacitive leads 391a and 391b; a tunneling junction connects a distal end of powered lead 377 to the most recessed area of quantum dot 373.

Figure 19:
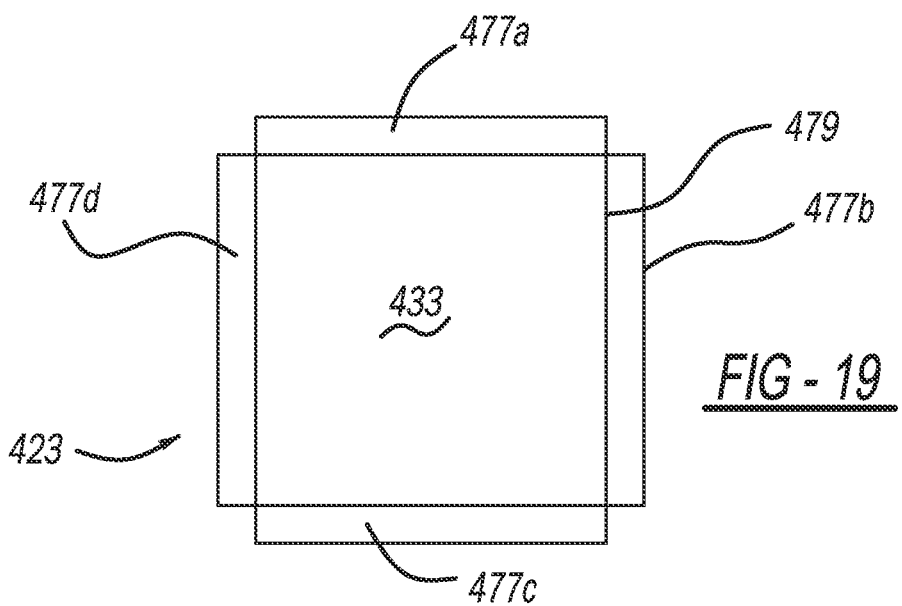
FIG. 19 is an enlarged end elevation view showing a third alternate embodiment of the probe of the present apparatus.

Finally, FIG. 19 illustrates yet another alternate embodiment probe 423 of the present apparatus. This exemplary probe 423 has a generally polygonal cross-section adjacent a quantum dot 473, preferably rectangular or square, with at least four flat sidewalls 479. Tunneling electrical leads 477a, 477b, 477c and 477d are deposited on each flat sidewall and are peripherally spaced apart from each other at the sidewall intersections or corners. Tunneling junctions connect the tunneling leads 477a-d to either the preferred centrally asymmetrically tapered version or alternately a curved or non-tapered (e.g., perpendicular to a longitudinal centerline) version of quantum dot 273. Alternately, one or more of the leads in this polygonal configuration can be capacitive or backgate leads with associated capacitive or insulating junctions.

While various features of the present invention have been disclosed, it should be appreciated that other variations may be employed. For example, different peripheral shapes and sizes of the substrate, leads and junctions can be employed, although various advantages of the present system may not be realized. As another example, different microscopes, actuators, specimen holders and processing holders may be used, but certain benefits may not be obtained. Additionally, alternate electrical circuits, milling processes and deposition processes can be employed, although performance may differ. Features of each of the embodiments and uses may be interchanged and replaced with similar features of other embodiments, and all of the claims may be multiply dependent on each other in any combination. Variations are not to be regarded as a departure from the present disclosure, and all such modifications are intended to be included within the scope and spirit of the present invention.

The invention claimed is:

1. A microscope apparatus comprising a probe which further comprises:
    an insulating substrate having a centerline;
    a quantum dot located on an end of the substrate;
    a first electrical lead located on a side portion of the substrate;
    at least a second electrical lead located on another side portion of the substrate, the electrical leads being spaced apart from each other on the substrate; and
    a tunneling junction located between and adjacent to the first electrical lead and a first area of the quantum dot;
    the quantum dot being offset angled from a plane perpendicular to the centerline with the first area of the quantum dot: being more recessed than a second area of the quantum dot which intersects the centerline, and being more recessed than a third area of the quantum dot which is closest to the second electrical lead.

2. The apparatus of claim 1, wherein:
    the substrate is an elongated glass fiber;
    the electrical leads and the quantum dot are metallic; and
    the tunneling junction is a metallic oxide at a distal end of the electrical lead.

3. The apparatus of claim 1, further comprising a substantially insulating junction located between the third area of the quantum dot and the second electrical lead, the insulating junction being longer, of smaller cross-sectional area and less conductive than the tunneling junction.

4. The apparatus of claim 1, wherein the end of the substrate and a specimen-facing surface of the quantum dot are both asymmetrical and tilted such that the entire specimen-facing surface of the quantum dot is 95-99° offset angled relative to the centerline of the substrate, and the substrate is an elongated glass fiber.

5. The apparatus of claim 1, wherein:
    the first electrical lead is connected to a power source;
    the second electrical lead is part of a capacitive circuit and electrons from the first electrical lead and the quantum dot are prevented from flowing to the at least second electrical lead; and
    an electrical field of the quantum dot is sensed by the capacitive circuit.

6. The apparatus of claim 1, further comprising:
    a holder aligned with the centerline of the substrate;
    at least one actuator operably causing movement of at least one of: the holder or the probe, while they are aligned; and
    a specimen retained by the holder, the specimen being located less than 20 nm from the quantum dot, with the third area of the quantum dot being closer to the specimen than the first area of the quantum dot.

7. The apparatus of claim 1, further comprising:
    a holder aligned with the centerline of the substrate; and
    a specimen retained by the holder, the specimen being located less than 1 nm from the quantum dot, with the third area of the quantum dot being closer to the specimen than the first area of the quantum dot.

8. The apparatus of claim 1, further comprising a specimen located close enough to the quantum dot to create a strong-coupling between the probe and the specimen, and create probe hybridization with electronic states in the specimen, while allowing for single electron counting and angstrom distance tunneling.

9. The apparatus of claim 1, wherein:
    an exterior surface of the quantum dot is substantially flat and tapered from the first area closest to the tunneling junction to the third area which is on an opposite side of the quantum dot;
    a periphery of the quantum dot being substantially circular; and
    the side portions of the substrate, upon which the lead are located, are part of a substantially frusto-conical surface at the end of a substantially cylindrical, transparent and elongated shaft of the substrate.

10. The apparatus of claim 1, wherein:
    the first electrical lead is connected to a power source; and
    the at least second electrical lead includes a capacitive lead and a backgate lead, which are circumferentially spaced apart from each other, and electrons from the first electrical lead and the quantum dot are prevented from flowing to the capacitive lead.

11. The apparatus of claim 1, wherein the substrate of the probe has a substantially polygonal cross-sectional shape adjacent the quantum dot, with the electrical leads being on different and substantially flat sidewalls of the substrate.

12. The apparatus of claim 1, further comprising:
    a specimen holder adjacent the quantum dot;
    a scanning head retaining the probe;
    the substrate of the probe being an elongated glass fiber;
    a sorption pump coupled to the head;
    a cryogenic housing within which the head, the probe and the holder are located, a vacuum pressure being inside of the housing;
    the first lead being metallic and thinner than the second lead which is also metallic, both leads being spaced apart from each other on surfaces of the substrate which are offset angled from the centerline; and
    a substantially insulating junction located between the quantum dot and the second electrical lead, the insulating junction being longitudinally longer and less conductive than the tunneling junction.

13. The apparatus of claim 1, further comprising a quantum computer within which the probe is located.

14. A microscope apparatus comprising a probe which further comprises:
    an elongated glass fiber;
    a nanoscale semiconductor located on a tip of the fiber;
    a metallic, tunneling electrical lead located on the fiber and being connected to a power source;
    a metallic, capacitive electrical lead located on the fiber and being peripherally spaced apart from the tunneling electrical lead; and
    a tunneling junction located between the first electrical lead and a first area of the nanoscale semiconductor, the tunneling junction being metallic oxide;
    a capacitive junction located between the nanoscale semiconductor and the capacitive electrical lead, the capacitive junction being metallic oxide and less conductive than the tunneling junction;
    the capacitive junction being longer than the tunneling junction; and
    the tunneling junction being recessed more than the capacitive junction.

15. The apparatus of claim 14, wherein the tip of the substrate and the nanoscale semiconductor are asymmetrical and tilted such that an entire exterior surface of the nanoscale semiconductor is 95-99° offset angled relative to an elongated centerline of the fiber.

16. The apparatus of claim 14, further comprising:

electrons from the tunneling electrical lead and the nanoscale semiconductor being prevented from flowing to the capacitive electrical lead; and an electrical field of the nanoscale semiconductor being sensed by a capacitive circuit of which the capacitive lead is a part.

17. The apparatus of claim 14, further comprising:

a holder adjacent the probe;

at least one actuator operably causing movement of at least one of: the holder or the probe;

a specimen retained by the holder, the specimen being located less than 1 nm from the nanoscale semiconductor; and a strong-coupling being created between the probe and the specimen, while allowing for single electron counting and angstrom distance tunneling.

18. The apparatus of claim 1, wherein the nanoscale semiconductor is a quantum dot, an exterior surface of which is substantially flat and tapered from a first peripheral point closest to the tunneling junction to an opposite peripheral point closest to the capacitive junction.

19. A method of manufacturing a probe, the method comprising:

(a) etching a substantially conical end on an elongated glass fiber;

(b) creating a tapered surface on the etched end of the fiber with a focused ion-beam;

(c) creating metallic leads on a remaining frusto-conical sidewall of the fiber; and (d) creating a metallic quantum dot on the tapered surface of the fiber.

20. The method of claim 19, further comprising:

creating a metallic oxide tunneling junction adjacent the end of the fiber between a first of the leads, connectable to a power source, and the quantum dot;

creating an insulating junction adjacent the end of the fiber between a second of the leads, which is part of a capacitive circuit, and the quantum dot; and causing the insulating junction to be less conductive than the tunneling junction, the second lead and the quantum dot.

21. The method of claim 19, wherein the tapered surface of the fiber and a specimen-facing surface of the quantum dot are more recessed closest to a tunneling junction and longitudinally extend the furthest closest to a capacitive junction.

22. The method of claim 19, further comprising rounding a peripheral exterior corner of the quantum dot adjacent a tunneling junction, the tunneling junction being located between the quantum dot and a first of the leads which is connectable to a power source.

23. The method of claim 19, further comprising placing the probe in a cryogenic vacuum of a scanning microscope, within 1.0 nm of a specimen to create a strong-coupling quantum interaction between the probe and the specimen.

* * * * *